(12) United States Patent
Nakagawa

(10) Patent No.: US 10,570,903 B2
(45) Date of Patent: Feb. 25, 2020

(54) CENTRIFUGAL PUMP

(71) Applicant: Kabushiki Kaisha Saginomiya Seisakusho, Nakano-ku, Tokyo (JP)

(72) Inventor: Taiki Nakagawa, Sayama (JP)

(73) Assignee: KABUSHIKI KAISHA SAGINOMIYA SEISAKUSHO, Tokyo (JP)

(*) Notice: Subject to any disclaimer, the term of this patent is extended or adjusted under 35 U.S.C. 154(b) by 644 days.

(21) Appl. No.: 14/995,402

(22) Filed: Jan. 14, 2016

(65) Prior Publication Data

US 2016/0208805 A1 Jul. 21, 2016

(30) Foreign Application Priority Data

Jan. 17, 2015 (JP) .................. 2015-007306

(51) Int. Cl.
| | |
|---|---|
| *F04D 13/02* | (2006.01) |
| *F04D 13/06* | (2006.01) |
| *F04D 29/048* | (2006.01) |
| *A61M 1/10* | (2006.01) |
| *F04D 29/42* | (2006.01) |

(52) U.S. Cl.
CPC ......... *F04D 13/026* (2013.01); *A61M 1/1015* (2014.02); *F04D 13/024* (2013.01); *F04D 13/0606* (2013.01); *F04D 13/0633* (2013.01); *F04D 29/048* (2013.01); *F04D 13/064* (2013.01); *F04D 29/426* (2013.01)

(58) Field of Classification Search
CPC ............... F04D 13/026; F04D 13/0606; F04D 13/0633; F04D 29/048; F04D 29/4266; F04D 29/426; F04D 13/024; F04D 13/0666; A61M 1/101; A61M 1/1015
See application file for complete search history.

(56) References Cited

U.S. PATENT DOCUMENTS

| | | | |
|---|---|---|---|
| 2,970,548 A * | 2/1961 | Vilhelm Berner Sven Gustav ..... | H02K 5/128 310/104 |
| 6,082,974 A * | 7/2000 | Takemoto ........... | F04D 15/0066 417/366 |
| 2014/0205480 A1* | 7/2014 | Nakano ............... | F04D 29/4293 417/420 |

FOREIGN PATENT DOCUMENTS

JP H10-9185 A 1/1998

* cited by examiner

*Primary Examiner* — Peter J Bertheaud
(74) *Attorney, Agent, or Firm* — Snyder, Clark, Lesch & Chung, LLP

(57) ABSTRACT

A centrifugal pump includes: a rotating blade member including an impeller member and a rotor magnet associated with the impeller member, a main body casing in which the rotating blade member is accommodated, a coil portion that rotates the rotating blade member, wherein the coil portion is located on a periphery of the rotor magnet, and an axial member which is associated with the main body casing, wherein the rotating blade member pivots around the axial member. A clearance, in which the rotor magnet is allowed to move, is provided between the blade member and the rotor magnet.

6 Claims, 8 Drawing Sheets

CENTRIFUGAL PUMP

TECHNICAL FIELD

Embodiments relate to a centrifugal pump to circulate the fluid in the closed circuit, for instance, refrigerant used for refrigerant circulation circuits such as air conditioners and freezers, and cooling water, etc. used for cooling circulation circuits for parts, apparatuses, etc. that generate heat.

BACKGROUND ART

FIG. 7 shows vertical cross sectional view of such a conventional centrifugal pump.

As shown in FIG. 7, the conventional centrifugal pump 100 comprises a rotating blade member 102.

This rotating blade member 102 comprises a plurality of impeller members 106, which are radially extended toward the outer periphery, at an upper part of a circular tube bearing portion 104.

In addition, in the specification, the terms that indicate vertical directions, such as "upper side", "upper portion", "upper", "lower side", "lower portion", and "lower" indicate the vertical directions in each drawing.

Moreover, they indicate a relative position of each member and they do not indicate absolute positions.

The impeller member 106 includes abase end portion 108 which is extended upward from the bearing portion 104 toward the outer periphery, an enlarged diameter portion 110, of which diameter is enlarged upwardly toward the outer periphery from this base end portion 108, and an outside blade portion 112, which is extended from this enlarged diameter portion 110 toward the outer periphery.

Moreover, as for the rotating blade member 102, a rotor magnet 122, which includes a permanent magnet having an annular shape, is formed on the outer periphery of the base end portion 108.

Between the rotor magnet 122 and the impeller member 106, there is the structure that prevents the turn stop of the rotor magnet 122 and the fall of the rotor magnet 122 against the impeller member 106.

As a result, the impeller member 106 is rotated around an axial member 154 together with the rotor magnet 122.

Furthermore, as shown in FIG. 7, the centrifugal pump 100 includes a main body casing 124 in which the rotating blade member 102 is accommodated.

The main body casing 124 includes an upper main body casing 126.

The upper main body casing 126 comprises a top wall 128 and a side peripheral wall 130 which is downwardly extended from an outer periphery of the top wall 128.

On the side peripheral wall 130 of the upper main body casing 126, a suction side coupling member 132 (sucking side pipe) is fixed in a sealed state.

As a result, the suction side coupling member 132 is connected to the main body casing 124.

Moreover, on the side peripheral wall 130 of the upper main body casing 126, to oppose to the suction side coupling member 132, a discharge side coupling member 136 (discharge side pipe) is fixed in a sealed state.

As a result, the discharge side coupling member 136 is connected to the main body casing 124.

Moreover, as shown in FIG. 7, the main body casing 124 includes a lower main body casing 138 (rotor casing).

Moreover, on an inner wall of a lower end part 141 of the side peripheral wall 130 of the upper main body casing 126, an outer periphery flange 142 of the lower main body casing 138 is fixed in a sealed state.

As a result, in the main body casing 124, an interior space S1, which is surrounded with the upper main body casing 126 and the lower main body casing 138, is formed.

As shown in FIG. 7, this lower main body casing 138 includes a blade accommodating portion 144, which is extended horizontally from an outer periphery flange 142 of the lower main body casing 138 to inner periphery side, and a rotor magnet accommodating portion 146, which is extended downwardly from this blade accommodating portion 144.

In addition, under this rotor magnet accommodating portion 146, a lower bearing member accommodating portion 148, which is of cylindrical shape having a bottom, is formed.

Moreover, in the lower bearing member accommodating portion 148, a lower bearing member 150 is fitted by, for instance, press fit, etc.

In a shaft hole 152 formed in this lower bearing member 150, a lower end portion 156 of an axial member 154 is fixed as pivoted.

Moreover, in the bearing portion 104 of this rotating blade member 102, the axial member 154 passes through so that the rotating blade member 102 can be rotated around the axial member 154.

In addition, the main body casing 124 is provided with a blade casing 158.

This blade casing 158, on the side of the suction side coupling member 132, an outer periphery flange 160 of this blade casing 158 is fixed in a sealed state under the side peripheral wall 130 of the upper main body casing 126.

On the other hand, as for the blade casing 158, an opening portion is formed to the side peripheral wall 162 on the side of the discharge side coupling member 136.

The periphery of the opening portion of this side peripheral wall 162 is fixed to the side peripheral wall 130 of the main body casing 124 in a sealed state together with the discharge side coupling member 136.

Moreover, the blade casing 158 includes a side peripheral wall 162, which is upwardly extended from the outer periphery flange 160, and an extending portion 164, which is extended in the horizontal direction from the side peripheral wall 162 along the outside blade portion 112 of the impeller member 106.

By having such shape, between the blade casing 158 and the blade accommodating portions 144 of the lower main body casing 138, the impeller member 106 can be accommodated.

Moreover, to a protruding portion 128a, which is projected downwardly to a central portion of the top wall 128 of the upper main body casing 126, an upper bearing member 168 is fixed by a fixing holder 161, so that it is protruded downwardly in an inner periphery side opening portion 164a of an extending portion 164 of the blade casing 158.

On a shaft hole 170 formed in the upper bearing member 168, a top portion 172 of the axial member 154 that passes through an inside of the bearing portion 104 of the rotating blade member 102 is fixed as pivoted.

Moreover, by the blade casing 158, the interior space S1, which is formed by the upper main body casing 126 and the lower main body casing 138 is partitioned.

Consequently, a fluid introducing passage 174 is formed in the upper part.

Moreover, a rotating accommodating space S2, in which the rotating blade member 102 is accommodated, is formed in the lower part.

Moreover, as shown in FIG. 7, in the conventional centrifugal pump 100, a coil portion 204 is disposed on the outer periphery of the rotor magnet accommodating portion 146 of the lower main body casing 138 to be located on the periphery of the rotor magnet 122.

In addition, the coil portion 204 which rotates the rotating blade member 102 is provided.

As for the coil portion 204, a plurality of coils 210, which comprise a winding wire 208 rolled in a bobbin casing 206, are disposed in the circumferential direction at predetermined spaces.

In addition, these coils 210, in a coil cover main body 214 having the substantially cylindrical shape, are provided such that they are fitted to the outer periphery of the rotor magnet accommodating portion 146 of the lower main body casing 138 of the main body casing 124.

Moreover, as shown in FIG. 7, a main body casing side fixing bracket 186 is engaged with a coil side fixing protruded portion 216.

Consequently, the coil cover main body 214, in which the coil portion 204 is accommodated, can be provided detachably under the main body casing 124.

In addition, in FIG. 7, the reference numeral 226 indicates a connector, 228 indicates a lead line, and 230 indicates a magnetic pole sensor to detect the direction of the rotation and the position where the rotor magnet 122 is rotated.

In the conventional centrifugal pump 100 configured like this, the electric current flows through the coil 210 of the coil portion 204, so that the coil 210 is excited.

As a result, it effects on the rotor magnet 122 of the rotating blade member 102.

Consequently, the rotating blade member 102 can be rotated around the axial member 154, which passes through the bearing portion 104.

As a result, the fluid sucked from the suction side coupling member 132 passes from the fluid introducing passage 174, which is formed by the blade casing 158 and the upper main body casing 126, to the inner periphery side opening portion 164a of the extending portion 164 of the blade casing 158.

Moreover, the fluid that passes through the inner periphery side opening portion 164a is introduced into the rotating accommodating space S2, which is formed by the blade casing 158 and the lower main body casing 138.

In addition, by the turning force of the impeller member 106 of the rotating blade member 102, the fluid introduced into the rotating accommodating space S2 is discharged through the discharge side coupling member 136 from the rotating accommodating space S2 of the main body casing 124.

REFERENCE

[Patent Document 1]
 JP H10 (1998)-9185, A

SUMMARY

Problems to be Solved

By the way, such conventional centrifugal pump 100 is used for the system that assists cooling of heat generating parts and apparatuses or the like by using the circulation of the fluid for instance.

Moreover, there is a case in which it is used for not only the industrial use but also home apparatus (consumer electronics) according to the usage of the system that is built in.

Recently, as for home apparatus, the miniaturization and noise reduction are advanced.

In order to achieve this, a similar specification is required about the pump in which circulation of fluid is performed.

However, when the pump operates under a dry environment in which the fluid does not contain moisture, etc., the abnormal sound might be generated for instance.

In this case, the sound character of the generated abnormal sound is a resonance sound, and the entire main body of the centrifugal pump 100 is vibrated during the generation of the abnormal sound.

The generation of this abnormal sound does not depend on the voltage, and it is generated even if the voltage is decreased.

The mechanism of the generation of this abnormal sound occurs due to the cause as shown in FIG. 8.

In the conventional centrifugal pump 100 of FIG. 8, for convenience sake of the clarification, the coil 210 of the coil portion 204 is simplified as shown in the figure.

Moreover, the composition member of the coil cover main body 214, etc. is omitted and shown in the figure.

As shown in FIG. 8, when an electrical current is supplied, the rotor magnet 122 is drawn to the coil 210 of the coil portion 204 as shown by arrow F.

Therefore, against the coil 210 that is in the excitation phase, the rotating blade member 102 including the rotor magnet 122 and the impeller member 106 is tilted and rotated around a rotation central axis O', which is inclined against a rotation central axis O.

As a result, an inside diameter side 106a of the upper part of the impeller member 106 of the rotating blade member 102 comes in contact with the axial member 154 at T1 point which is enclosed with the circle shown in FIG. 8

Moreover, the lower end of the bearing portion 104 of the rotating blade member 102 comes in contact with the top of the lower bearing member 150 at T2 point which is enclosed with the circle shown in FIG. 8.

Under such a condition, as shown in FIG. 8, the rotating blade member 102 including the rotor magnet 122 and the impeller member 106 swing and rotate as shown by the chain line in FIG. 8.

As a result, it is considered that the state which comes in contact by two points (T1 and T2) is generated along with the rotation of the rotating blade member 102, and the abnormal sound (resonance sound) is generated.

Therefore, as shown in G portion enclosed with the circle in FIG. 8, the clearance E between the inside diameter side 106a of the impeller member 106 of the rotating blade member 102 and the outer periphery of the axial member 154 is narrowed.

As a result, the inclination (swinging) of the rotating blade member 102 shown in FIG. 8 is prevented.

Consequently, it is considered that the contact in the T1 point and the T2 point is controlled and the generation of the abnormal sound is prevented.

However, the dimension control of the clearance, the clearance E is, for instance, management of about 0.01-0.03 mm.

As a result, the demanded accuracy of parts is extremely high, high cost is required. Actually, it is difficult to achieve such a dimension control.

Moreover, in Patent Document 1 (JP H10 (1998)-9185, A), it is disclosed that the noise of the overall vibration generated from the pump is reduced.

In Patent Document 1, the rotor magnet and the blade member are integral structures.

As a result, there is the structure that the blade member is rotated and inclined following the rotor magnet sucked to the stator coil.

Consequently, such an abnormal sound (resonance sound) is generated.

In addition, in Patent Document 1, the stator holding portion has a cylindrical shape, and the cover in which this end portion is covered is provided.

The stator storage portion is sealed, and it is the structure by which the noise is not transmitted outside directly.

That is, in Patent Document 1, it has a structure in which the source of the vibration (sound) is not covered, but the whole portion is covered to improve the noise.

On the contrary, as described later, in the centrifugal pump disclosed here, the source of such an abnormal sound (mechanism) itself is improved by forming the clearance in which the rotor magnet can be moved between the blade member and the rotor magnet.

As a result, the generation of the abnormal sound is prevented.

Considering such a current state, whole portion is not covered to improve the noise and the source of the abnormal sound (mechanism) itself is improved.

As a result, the generation of the abnormal sound can be prevented.

Furthermore, a centrifugal pump, of which the durability and quietness are superior, and eccentricity of the blade member is not caused, is provided and the predetermined objective pump performance can be retained.

Solution to Problem

A centrifugal pump comprises:
a rotating blade member including an impeller member and a rotor magnet associated with the impeller member,
a main body casing in which the rotating blade member is accommodated, and
a coil portion that rotates the rotating blade member, wherein the coil portion is located on a periphery of the rotor magnet,
an axial member which is associated with the main body casing, wherein the rotating blade member pivots around the axial member,
wherein a clearance, in which the rotor magnet can be moved, is provided between the impeller member and the rotor magnet.

Where the clearance between the rotating blade member and the axial member is large, the rotor magnet is rotated while being drawn to the stator coil.

As a result, the rotor magnet cannot be rotated with sustaining the concentricity.

Consequently, the rotating blade member, which rotates with the rotor magnet, also follows to the movement of the rotor magnet, and it is rotated eccentrically.

Therefore, the rotating blade member comes in contact with the axial member, and the abnormal sound is generated.

On the contrary, by the configuration as stated above, the clearance, in which the rotor magnet can be moved, is formed between the impeller member and the rotor magnet.

As a result, swinging of the rotor magnet can be absorbed.

That is, a little clearance (i.e. backlash) is provided between the rotor magnet and the impeller member.

As a result, the load, by which the rotor magnet is drawn to the coil, is not transmitted to the impeller member.

Consequently, the impeller member itself is not inclined.

Therefore, the impeller member is not contacted to the axial member and the main body casing.

As a result, the durability and quietness is superior, and eccentricity of the impeller member is not caused, and the predetermined objective pump performance can be retained.

Moreover, it has the configuration in which the rotor magnet can be moved.

As a result, even if there is the state that the foreign matter is invaded and bitten between the rotor magnet and the main body casing, the rotor magnet can be moved along with the rotation of the rotating blade member.

Consequently, this bite state can be released instantaneously.

Therefore, the lock state, in which the rotating blade member cannot be rotated by the bite with the foreign matter, can be prevented.

Moreover, the centrifugal pump is characterized in that the clearance between the impeller member and the rotor magnet is a radial clearance between the impeller member and the rotor magnet.

Thus, if the clearance between the impeller member and the rotor magnet is a radial clearance between the impeller member and the rotor magnet, swinging of the rotor magnet can be absorbed by this radial clearance.

Moreover, the centrifugal pump is characterized in that the clearance between the impeller member and the rotor magnet is an axial clearance between the impeller member and the rotor magnet.

Thus, if the clearance between the impeller member and the rotor magnet is an axial clearance between the impeller member and the rotor magnet, swinging of the rotor magnet can be absorbed by this axial clearance.

Moreover, the centrifugal pump is characterized in that the clearance between the impeller member and the rotor magnet includes a radial clearance r between the impeller member and the rotor magnet, and an axial clearance h between the impeller member and the rotor magnet, and
is set to have the relation of r<h.

Thus, the relation between;
the radial clearance r between the impeller member and the rotor magnet; and
the axial clearance h between the blade member and the rotor magnet
is set to the relation of r<h.

As a result, the movement of the rotor magnet (i.e. inclination) is absorbed by the axial clearance h.

Consequently, the movement of the rotor magnet (inclination) is not transmitted to the blade member.

As a result, the impeller member itself is not inclined by following to the movement of the rotor magnet.

Therefore, the impeller member is not contacted to the axial member and the main body casing, and the durability and the silence property is superior, and eccentricity of the impeller member is not caused, and the predetermined objective pump performance can be retained.

Moreover, the centrifugal pump is characterized in that a dropout preventing means to prevent the impeller member and the rotor magnet from dropping out, is included.

By the configuration like this, since the dropout preventing means is included, the impeller member and the rotor magnet are prevented from dropping out.

As a result, the abnormal sound is not generated, and the rotation of the rotor magnet can surely be transmitted to the impeller member.

Moreover, a moderate clearance (backlash) can be formed between the impeller member and the rotor magnet.

As a result, the load, by which the rotor magnet is drawn to the coil, is not transmitted to the impeller member.

Consequently, the impeller member itself is not inclined, and the impeller member is not contacted to the axial member and the main body casing, and the durability and quietness is superior, and eccentricity of impeller member is not caused, and the predetermined objective pump performance can be retained.

Moreover, the centrifugal pump is characterized in that the main body casing has a first end a second end in an axial direction of the axial member, and the axial member is fixed at the first end and the second end.

Moreover, the centrifugal pump is characterized in that the main body casing has a third end at a side of the rotor magnet, and the axial member is fixed at the third end.

Advantageous Effects

According to the embodiments, the clearance, in which the rotor magnet can be moved, is formed between the impeller member and the rotor magnet.

As a result, swinging of the rotor magnet can be absorbed.

That is, a little clearance (i.e. backlash) is provided between the rotor magnet and the impeller member.

As a result, the load, by which the rotor magnet is drawn to the coil, is not transmitted to the impeller member.

Consequently, the impeller member itself is not inclined.

Therefore, the impeller member is not contacted to the axial member and the main body casing.

As a result, the durability and the silence property are superior, and eccentricity of the impeller member is not caused, and the predetermined objective pump performance can be retained.

Moreover, in the configuration, the rotor magnet can be moved.

As a result, even if there is the state that the foreign matter is invaded and bitten between the rotor magnet and the main body casing, the rotor magnet can be moved along with the rotation of the rotating blade member.

Consequently, this bite state can be released instantaneously.

Therefore, the lock state, in which the rotating blade member cannot be rotated by the bite with the foreign matter, can be prevented.

DESCRIPTION OF EMBODIMENTS

Figure 1:
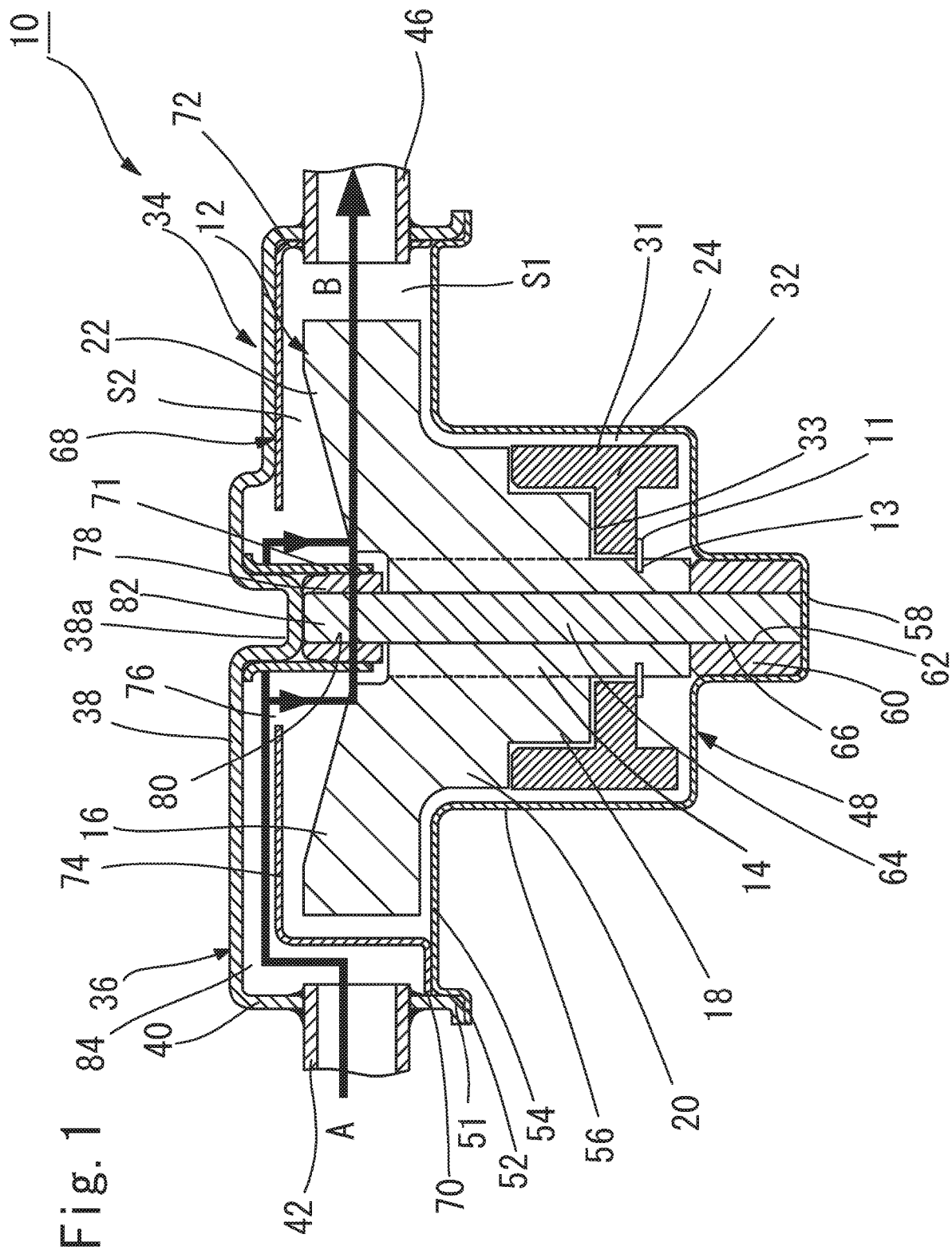
FIG. 1 is a vertical cross sectional view of the centrifugal pump.

Hereafter, embodiments are described in the detail or more on the basis of the drawing.

Embodiment 1

FIG. 1 is a vertical cross sectional view of the centrifugal pump.

Figure 2:
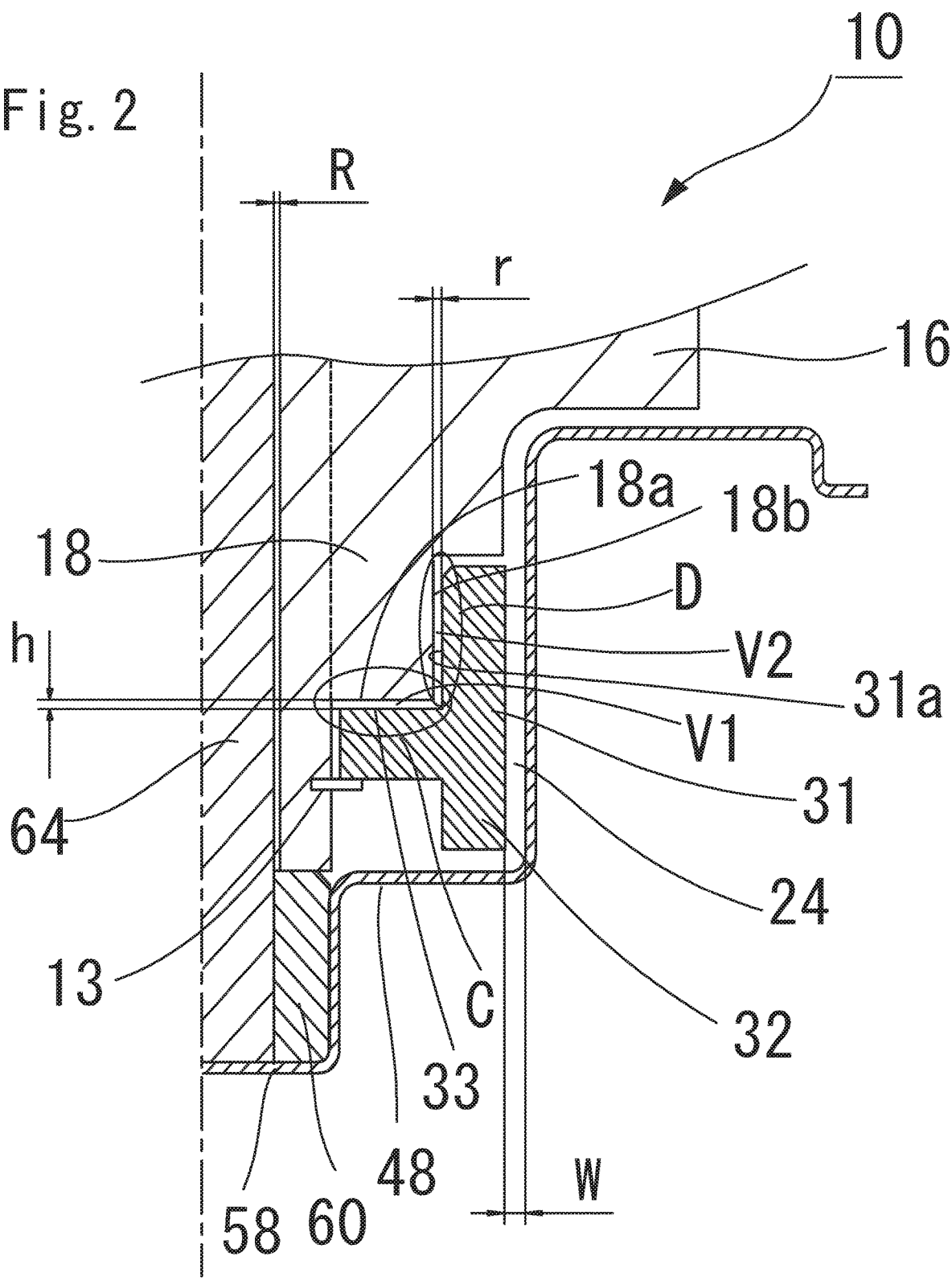
FIG. 2 is a partially enlarged cross sectional view of FIG. 1.

FIG. 2 is a partially enlarged sectional view of FIG. 1.

In FIG. 1, reference numeral 10 indicates a centrifugal pump as a whole.

Figure 7:
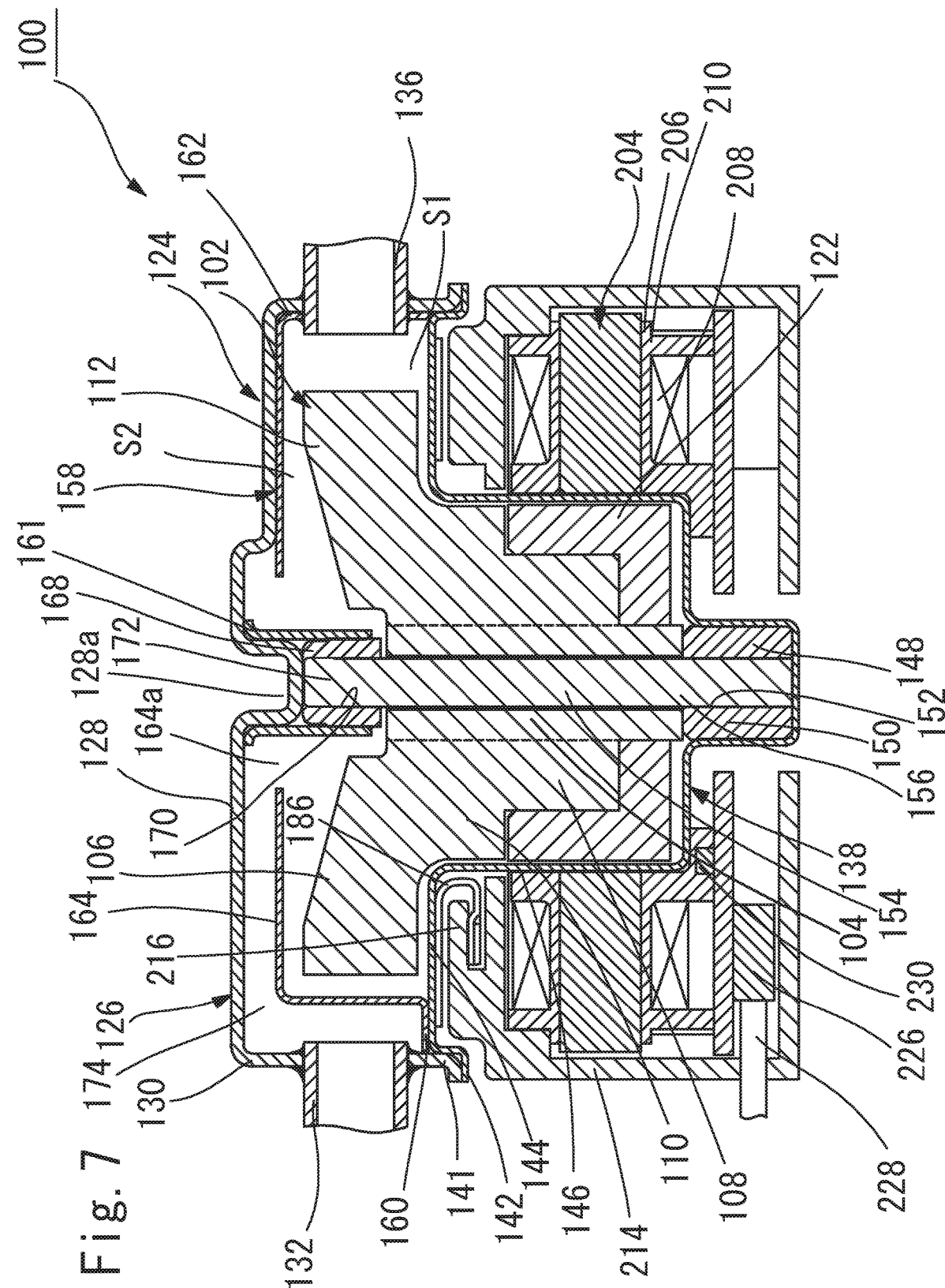
FIG. 7 is a vertical cross sectional view of the conventional centrifugal pump.

In the centrifugal pump 10 of FIG. 1, for convenience sake of clarification, a composition member such as the coil portion 204, which is located on the periphery of the rotor magnet 122, as described in the conventional centrifugal pump 100 shown in FIG. 7, and is disposed on the outer periphery of the rotor magnet accommodating portion 146 of the lower main body casing 138, and rotates the rotating blade member 102, is omitted and shown in the drawing.

As shown in FIG. 1, the centrifugal pump 10 comprises a rotating blade member 12.

This rotating blade member 12 comprises a plurality of impeller members 16, which are radially extended toward the outer periphery at an upper part of a circular tube bearing portion 14.

In addition, the number of impeller members 16 may be elected according to the usage of centrifugal pump 10 and the pump ability that is required, and is not limited particularly.

As shown in FIG. 1, the impeller member 16 includes a base end portion 18 which is extended toward the outer periphery of the bearing portion 14, an enlarged diameter portion 20, which is enlarged upwardly toward the outer periphery from this base end portion 18, and an outside blade portion 22, which is extended from this enlarged diameter portion 20 toward the outer periphery.

By forming the shape of the impeller member 16 like this shape, the discharge ability can be improved by the outside blade portion 22's function caused by rotation of the impeller member 16.

Moreover, on the rotating blade member 12, a rotor magnet accommodating portion 24, which is extended toward the outer periphery, is formed under the bearing portion 14.

In addition, a rotor magnet 32, which includes an annular permanent magnet, is fitted to the rotor magnet accommodating portion 24.

In addition, this rotor magnet 32 includes a component described below as a dropout preventing means to prevent the impeller member 16 and the rotor magnet 32 from dropping out.

That is, as shown in the enlarged view of FIG. 2, a groove 13, which is formed at the rotor magnet accommodating portion 24 of the impeller member 16, is provided, and a snap ring 11 is provided at this groove 13 and it is engaged.

As a result, the turn stop of the rotor magnet 32 and the fall of the rotor magnet 32 are prevented against the impeller member 16.

Consequently, the impeller member 16 is rotated around an axial member 64 together with the rotor magnet 32.

By the configuration like this, since the dropout preventing means (in this Embodiment, the groove 13 and the snap ring 11) is provided, the impeller member 16 and the rotor magnet 32 are prevented from dropping out.

As a result, the abnormal sound is not generated, and the rotation of the rotor magnet 32 can surely be transmitted to the impeller member 16.

Moreover, a moderate clearance (backlash) can be formed between the impeller member 16 and the rotor magnet 32.

As a result, the load, by which the rotor magnet 32 is drawn to the coil 210, is not transmitted to the impeller member 16.

Consequently, the impeller member 16 itself is not inclined, and the impeller member 16 is not contacted to the axial member 64 and the main body casing 34, and the durability and quietness is superior, and eccentricity of the impeller member 16 is not caused, and the predetermined objective pump performance can be retained.

In this case, as snap ring 11, for instance, the snap ring 11 having the ring C shape can be used.

Moreover, the material of the snap ring 11 is not particularly limited, and the metal and made of the plastic, etc. can be used.

Furthermore, as shown in FIG. 1, the centrifugal pump 10 includes a main body casing 34 in which the rotating blade member 12 is accommodated.

The main body casing 34 includes an upper main body casing 36.

The upper main body casing 36 includes a top wall 38 and a side peripheral wall 40 which is downwardly extended from an outer periphery of the top wall 38.

Moreover, as shown in FIG. 1, on the side peripheral wall 40 of the upper main body casing 36, an opening portion to fix a suction side coupling member 42 is formed.

As shown in FIG. 1, the suction side coupling member 42 is fixed to the opening portion in a sealed state with, for instance, the welding, the soldering and the adhesion, etc.

As a result, the suction side coupling member 42 is connected to the main body casing 34.

On the side peripheral wall 40 of the upper main body casing 36, an opening portion to fix a discharge side coupling member 46 is formed.

As shown in FIG. 1, on this opening portion, the discharge side coupling member 46 is fixed in a sealed state with, for instance, the welding, the brazing and the adhesion, etc.

As a result, the discharge side coupling member 46 is connected to the main body casing 34.

Moreover, as shown in FIG. 1, the main body casing 34 is provided with a lower main body casing 48.

Moreover, on an inner wall of a lower end part 51 of the side peripheral wall 40 of the upper main body casing 36, an outer periphery flange 52 of the lower main body casing 48 is fixed in a sealed state with, for instance, the welding, the brazing and the adhesion, etc.

As a result, in the main body casing 34, an interior space S1, which is surrounded with the upper main body casing 36 and the lower main body casing 48, is formed.

As shown in FIG. 1, this lower main body casing 48 includes a blade accommodating portion 54, which is extended horizontally from an outer periphery flange 52 of the lower main body casing 48 toward inner periphery side, and a rotor magnet accommodating portion 56, which is extended downwardly from this blade accommodating portion 54.

In addition, under this rotor magnet accommodating portion 56, a lower bearing member accommodating portion 58, which is of a cylindrical shape having a bottom, is formed.

Moreover, in the lower bearing member accommodating portion 58, a lower bearing member 60 is fitted by, for instance, press fit, etc.

In a shaft hole 62 formed in this lower bearing member 60, a lower end portion 66 of an axial member 64 is fixed as pivoted by, for instance, press fit, etc.

Moreover, in the bearing portion 14 of this rotating blade member 12, the axial member 64 passes through so that the rotating blade member 12 can be rotated around the axial member 64.

In addition, as shown in FIG. 1, the main body casing 34 is provided with a blade casing 68.

An outer periphery flange 70 of this blade casing 68 is fixed in a sealed state with, for instance, the welding, the brazing and the adhesion, as sandwiched between a lower end part 51 of the upper main body casing 36 and an outer periphery flange 52 of the lower main body casing 48.

Moreover, the blade casing 68 includes a side peripheral wall 72, which is upwardly extended from the outer periphery flange 70, and an extending portion 74, which is extended inwardly in the horizontal direction from the side peripheral wall 72 along the outside blade portion 22 of the impeller member 16.

By having such a shape, between the blade accommodating portions 54 of the blade casing 68 and the lower main body casing 48, the impeller member 16 can be accommodated.

Moreover, to a protruding portion 38a, which is projected downwardly to a central portion of the top wall 38 of the upper main body casing 36, an upper bearing member 78 is fixed by a fixing holder 71, so that it is protruded downwardly in an inner periphery side opening portion 76 of an extending portion 74 of the blade casing 68.

On a shaft hole 80 formed in the upper bearing member 78, a top portion 82 of the axial member 64, which passes through an inside of the bearing portion 14 of the rotating blade member 12, for instance, by pressing fit, is fixed as pivoted.

Moreover, as shown in FIG. 1, the diameter of the side peripheral wall 72 of the blade casing 68 is formed smaller than the diameter of the side peripheral wall 40 of the upper main body casing 36.

In addition, the height of the side peripheral wall 72 of the blade casing 68 is formed smaller than the height of the side peripheral wall 40 of the upper main body casing 36.

As a result, by the blade casing 68, the interior space S1, which is formed by the upper main body casing 36 and the lower main body casing 48, is partitioned.

Consequently, a fluid introducing passage 84 is formed on the upper part.

Moreover, a rotating accommodating space S2, in which the rotating blade member 12 is accommodated, is formed on the lower part.

The centrifugal pump 10 configured like this is operated as follows.

First of all, the electric current is flowed through the coil 210 of the coil portion 204, so that the coil 210 is excited.

As a result, it effects on the rotor magnet 32 of the rotating blade member 12.

Consequently, the rotating blade member 12 can be rotated around the axial member 64, which passes through the bearing portion 14.

As a result, the rotating blade member 12 is rotated.

Consequently, as shown by arrow A of FIG. 1, the fluid sucked from the suction side coupling member 42 passes from the fluid introducing passage 84, which is formed by the blade casing 68 and the upper main body casing 36, to the inner periphery side opening portion 76 of the extending portion 74 of the blade casing 68.

Moreover, the fluid that passes through the inner periphery side opening portion 76 is introduced into the rotating accommodating space S2, which is formed by the blade casing 68 and the lower main body casing 48.

In addition, by the turning force of the impeller member 16 of the rotating blade member 12, as shown by arrow B of FIG. 1, the fluid introduced into the rotating accommodating space S2 is discharged through the discharge side coupling member 46 from the rotating accommodating space S2 of the main body casing 34.

Figure 8:
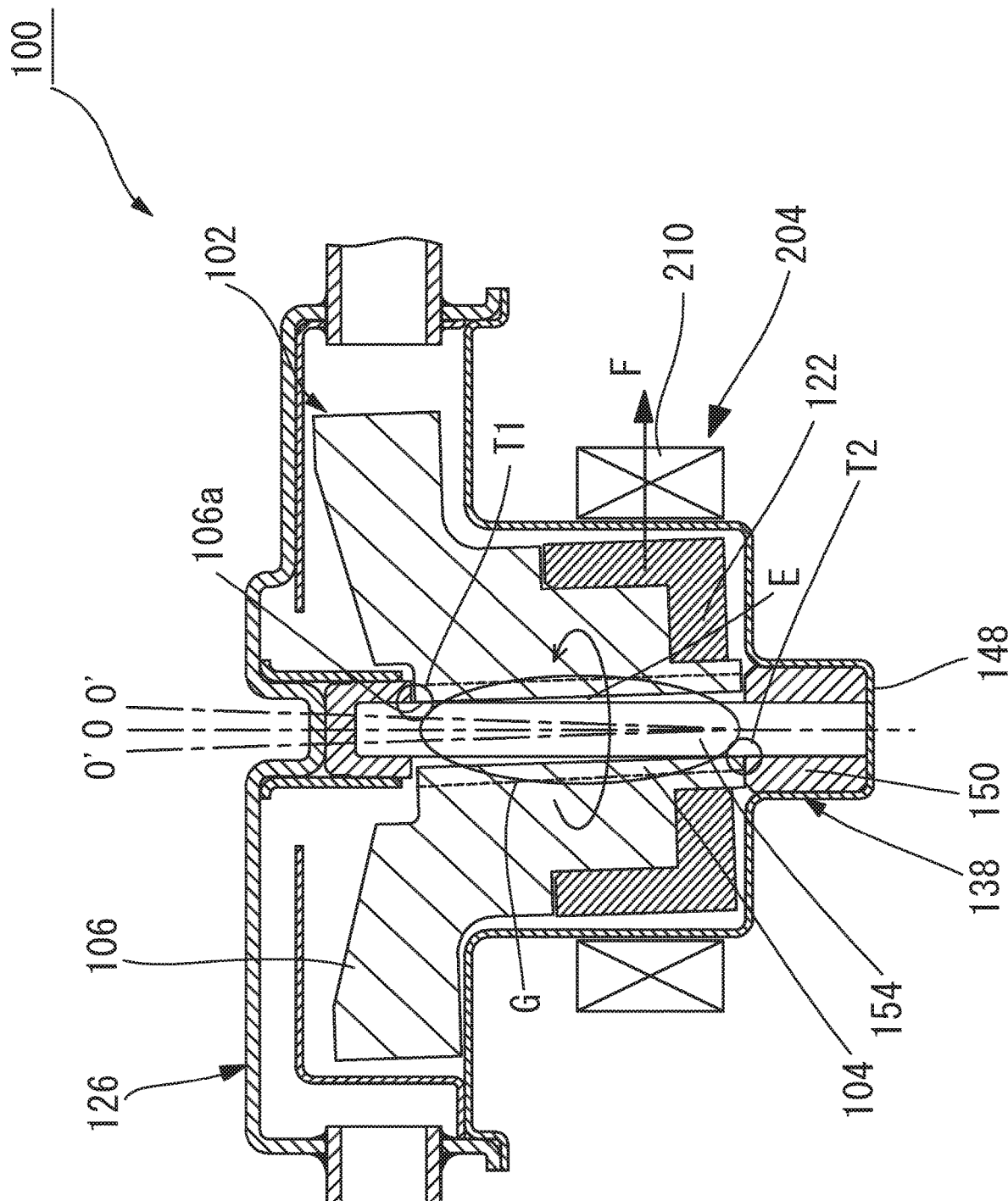
FIG. 8 is a vertical cross sectional view that shows the mechanism of the generation of the abnormal sound of the conventional centrifugal pump.

By the way, in the conventional centrifugal pump 100, as shown in FIG. 8, the rotating blade member 102 including the rotor magnet 122 and the impeller member 106 swings and rotates, as shown by the chain line in FIG. 8, in the contacting state by two points (T1 and T2).

As a result, the abnormal sound (resonance sound) is generated.

In order to prevent such swinging, in the centrifugal pump 10 of this Embodiment, as shown in FIG. 2, at the portion C and D enclosed with the circle of FIG. 2, a clearance, in which the rotor magnet 32 can be moved, is formed between the impeller member 16 and the rotor magnet 32.

That is, at the portion C enclosed with the circle of FIG. 2, between a lower end 18a of the base end portion 18 of the impeller member 16 and an upper surface 33 of the rotor magnet 32, an axial clearance V1 is formed.

Moreover, at the portion D enclosed with the circle of FIG. 2, between an inside diameter side 31a of an outer periphery cylindrical portion 31 which extends in an axial direction of the rotor magnet 32 and an outside diameter side 18b of the base end portion 18 of the impeller member 16, a radial clearance V2 between the impeller member 16 and the rotor magnet 32 is formed.

By configuring like this, between the impeller member 16 and the rotor magnet 32, the axial clearance V1 and the radial clearance V2 are formed, so that the clearance in which in the rotor magnet can be moved is formed.

Therefore, swinging of the rotor magnet 32 can be absorbed by the clearance, which includes the axial clearance V1 and the radial clearance V2.

That is, a little clearance (i.e. backlash) V1, V2 are provided between the rotor magnet 32 and the impeller member 16.

As a result, the load, by which the rotor magnet 32 is drawn to the coil, is not transmitted to the impeller member 16. Consequently, the impeller member 16 itself is not inclined.

Therefore, the impeller member 16 is not contacted to the axial member 64 and the main body casing 34 (the lower main body casing 48).

As a result, the durability and quietness are superior, and eccentricity of the impeller member 16 is not caused, and the predetermined objective pump performance can be retained.

Moreover, it has the configuration in which the rotor magnet 32 can be moved.

As a result, even if there is the state that the foreign matter is invaded and bitten between the rotor magnet 32 and the main body casing 34 (the lower main body casing 48), the rotor magnet 32 can be moved along with the rotation of the rotating blade member 12.

Consequently, this bite state can be released instantaneously.

Therefore, the lock state, in which the rotating blade member 12 cannot be rotated by the bite with the foreign matter, can be prevented.

Moreover, in this case, as shown by the enlarged view of FIG. 2, it is desirable that, the relation between a radial clearance r between the impeller member 16 and the rotor magnet 32; and an axial clearance h between the impeller member 16 and the rotor magnet 32 is set to the relation of $r<h$.

Thus, the relation between a radial clearance r between the impeller member 16 and the rotor magnet 32; and an axial clearance h between the impeller member 16 and the rotor magnet 32 is set to the relation of $r<h$.

As a result, the movement of the rotor magnet 32 (i.e. inclination) is absorbed by the axial clearance h.

Consequently, the movement of the rotor magnet 32 (inclination) is not transmitted to the impeller member 16.

As a result, the impeller member 16 itself is not inclined following to the movement of the rotor magnet 32.

Therefore, the impeller member 16 is not contacted to the axial member 64 and the main body casing 34 (the lower main body casing 48), and the durability and quietness is superior, and eccentricity of the impeller member 16 is not caused, and the predetermined objective pump performance can be retained.

Moreover, in this case, as shown by the enlarged view of FIG. 2, it is desirable that, the relation between a clearance R between the impeller member 16 and the axial member 64; the radial clearance r between the impeller member 16 and the rotor magnet 32; and a clearance W between the outer periphery and main body casing 34 (lower main body casing 48) of the rotor magnet 32 is set to the relation of $W>R+r$.

As a result, the effect of preventing the lock state, in which the rotating blade member 12 cannot be rotated by the bite with the foreign matter is superior.

Moreover, as shown by the enlarged view of FIG. 2, it is desirable that, the relation between the clearance R between the impeller member 16 and the axial member 64 and the radial clearance r between the impeller member 16 and the rotor magnet 32 is set to the relation of $R<r$.

Thus, the relation between the clearance R between the impeller member 16 and the axial member 64 and the radial clearance r between the impeller member 16 and the rotor magnet 32 is set to the relation of $R<r$.

As a result, the impeller member 16 is not contacted to the axial member 64, and swinging of the rotor magnet 32 can be absorbed by this radial clearance r.

That is, if the clearance R between the impeller member 16 and the axial member 64 is narrow, the inclination of the impeller member 16 is small.

However, the dimension control of the clearance is, for instance, management of about 0.01-0.03 mm.

As a result, the demanded accuracy of parts is extremely high, high cost is required. Actually, it is difficult to achieve such a dimension control.

Therefore, the radial clearance r between the impeller member 16 and the rotor magnet 32 is enlarged to the extent that the clearance R between the impeller member 16 and the axial member 64 cannot be narrowed.

As a result, inclination (Swinging) of the rotating blade member 12 is prevented, and contact of the impeller member 16 with the axial member 64 is controlled and the generation of the abnormal sound is prevented.

Embodiment 2

Figure 3:
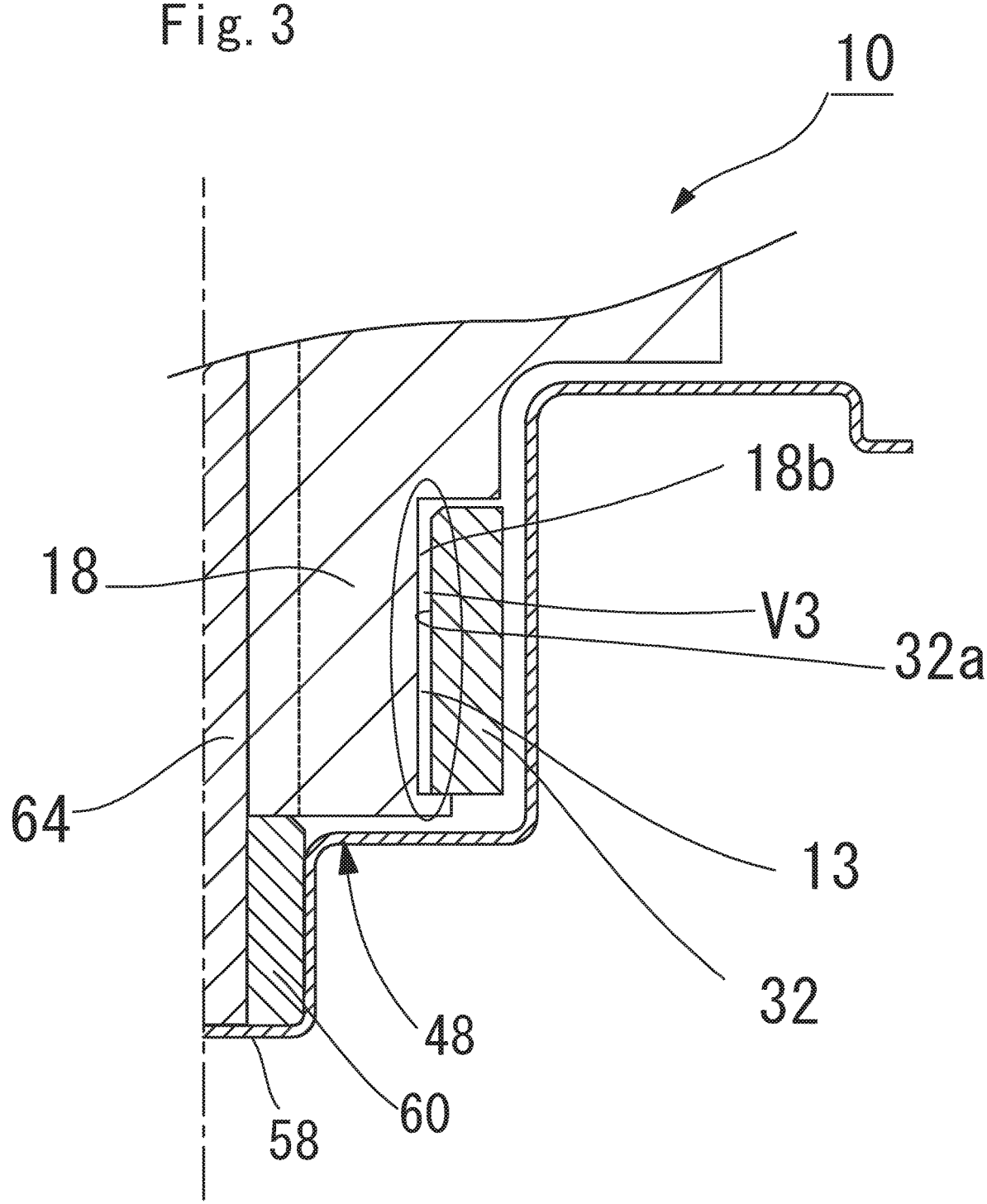
FIG. 3 is a partially enlarged cross sectional view, similar to FIG. 2, in which Embodiment 2 of the centrifugal pump is shown.

FIG. 3 is a partially enlarged cross sectional view similar to FIG. 2, in which Embodiment 2 of the centrifugal pump is shown.

The centrifugal pump 10 of this Embodiment includes basically similar composition of the Embodiment shown in FIG. 1-FIG. 2.

The same reference numerals refer to the same composition members, and the detailed explanation is omitted.

In the centrifugal pump 10 of Embodiment 1, between the impeller member 16 and the rotor magnet 32, the axial clearance V1 and the radial clearance V2 are formed.

However, in the centrifugal pump 10 of this Embodiment 2, the rotor magnet 32 is of a cylindrical shape.

Moreover, between the outside diameter side 18b of the base end portion 18 of the impeller member 16 and an inside diameter side 32a of the rotor magnet 32, only a radial clearance V3 is formed.

Thus, only the radial clearance V3 may be formed as a clearance, in which the rotor magnet 32 can be moved between the impeller member 16 and the rotor magnet 32.

As a result, swinging of the rotor magnet 32 can be absorbed by the clearance, which includes this radial clearance V3.

In the centrifugal pump 10 of Embodiment 1, as shown in FIG. 1, as for the rotor magnet 32, as the dropout preventing means to prevent the impeller member 16 and the rotor magnet 32 from dropping out, the groove 13, which is formed at the rotor magnet accommodating portion 24 of the impeller member 16, is provided, and the snap ring 11 is provided at this groove 13 and it is engaged.

As a result, the turn stop of the rotor magnet 32 and the fall of the rotor magnet 32 are prevented against the impeller member 16.

On the contrary, in the centrifugal pump 10 of this Embodiment, as shown in FIG. 3, as a dropout preventing means to prevent the impeller member 16 and the rotor magnet 32 from dropping out, the rotor magnet 32 having the cylindrical shape is fitted to the groove 13, which is formed on the outside diameter side 18b of the base end portion 18 of the impeller member 16 to correspond to the shape of the rotor magnet 32.

As a result, the turn stop of the rotor magnet 32 and the fall of the rotor magnet 32 are prevented against the impeller member 16.

Embodiment 3

Figure 4:
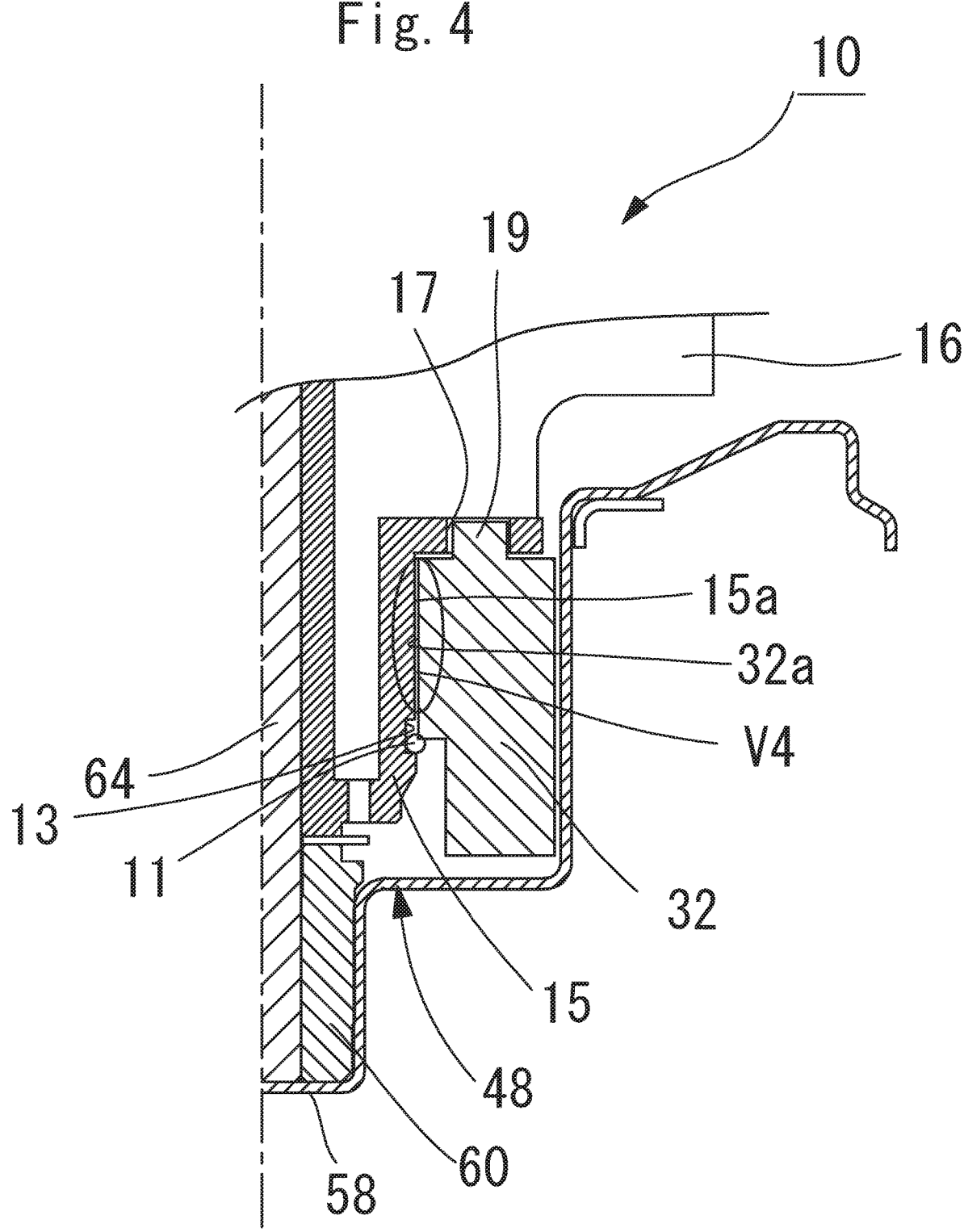
FIG. 4 is a partially enlarged cross sectional view, similar to FIG. 2, in which Embodiment 3 of the centrifugal pump.

FIG. 4 is a partially enlarged cross sectional view similar to FIG. 2 in which Embodiment 3 of the centrifugal pump is shown.

The centrifugal pump 10 of this Embodiment includes basically similar composition of the Embodiment 1 shown in FIG. 1-FIG. 2.

The same reference numerals refer to the same composition members, and the detailed explanation is omitted.

In the centrifugal pump 10 of Embodiment 1, as shown in FIG. 1, as for the rotor magnet 32, as the dropout preventing means to prevent the impeller member 16 and the rotor magnet 32 from dropping out, the groove 13, which is formed at the rotor magnet accommodating portion 24 of the impeller member 16, is provided, and the snap ring 11 is provided at this groove 13 and it is engaged.

As a result, the turn stop of the rotor magnet 32 and the fall of the rotor magnet 32 are prevented against the impeller member 16.

On the contrary, in the centrifugal pump 10 of this Embodiment, as shown in FIG. 4, as a dropout preventing means to prevent the impeller member 16 and the rotor magnet 32 from dropping out, the groove 13, which is formed at the rotor magnet accommodating portion 24 of the impeller member 16, is provided, and the snap ring 11 is provided at the groove 13 and it is engaged.

Furthermore, an engagement hole 17 is formed at the lower end of the base end portion 18 of the impeller member 16, and a protruding portion 19, which is formed on the top of the rotor magnet 32, is fitted to this engagement hole 17.

As a result, the rotation transmission portion is configured and the turn stop of the rotor magnet 32 and the fall of the rotor magnet 32 are prevented against the impeller member 16.

In addition, in case of this Embodiment, as shown in FIG. 4, as the snap ring 11, for instance, the snap ring 11 having the O-ring shape and including the elastic member such as rubber is used.

Moreover, as the snap ring 11, for instance, the snap ring 11 including a retaining ring, which has the spring and elasticity, and which is molded by metallic linear member in a ring C shape, may be used.

Like this, by including the snap ring 11 formed of the elastic member, even if the rotor magnet 32 is a fragile material, when the rotor magnet 32 is provided, the crack is not caused in the rotor magnet 32 due to the elasticity of the snap ring 11.

In addition, when the impeller member 16 and the rotor magnet 32 are rotated, the stress does not concentrate on this fixing portion, and the dropout can surely be prevented.

Moreover, in the centrifugal pump 10 of this Embodiment 3, as well as the centrifugal pump 10 of Embodiment 2, the rotor magnet 32 is of a cylindrical shape.

Moreover, between an outside diameter side 15a of a lower side 15 of the bearing portion 14 of the impeller member 16 and an inside diameter side 32a of the rotor magnet 32, only radial clearance V4 is formed.

As a result, swinging of the rotor magnet 32 can be absorbed by the clearance, which includes the radial clearance V4.

Embodiment 4

Figure 5:
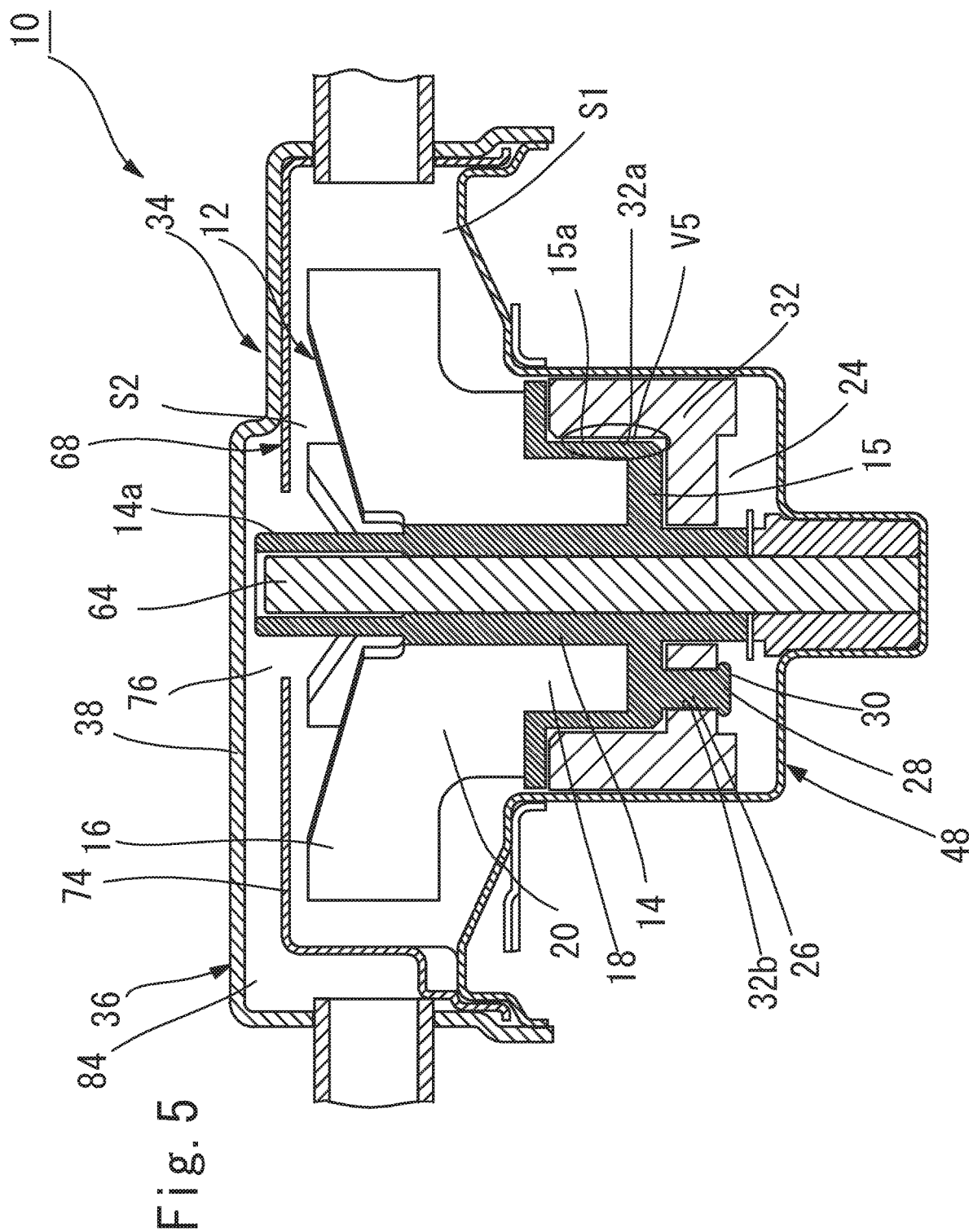
FIG. 5 is a vertical cross sectional view that shows Embodiment 4 of the centrifugal pump.

FIG. 5 is a vertical sectional view that shows Embodiment 4 of the centrifugal pump.

The centrifugal pump 10 of this Embodiment includes basically similar composition of the Embodiment 1 shown in FIG. 1-FIG. 2.

The same reference numerals refer to the same composition members, and the detailed explanation is omitted.

In the centrifugal pump 10 of Embodiment 1, as shown in FIG. 1, as for the rotor magnet 32, as the dropout preventing means to prevent the impeller member 16 and the rotor magnet 32 from dropping out, the groove 13, which is formed at the rotor magnet accommodating portion 24 of the impeller member 16, is provided, and the snap ring 11 is provided at this groove 13 and it is engaged.

As a result, the turn stop of the rotor magnet 32 and the fall of the rotor magnet 32 are prevented against the impeller member 16.

On the contrary, in the centrifugal pump 10 of this Embodiment, as a dropout preventing means to prevent the impeller member 16 and the rotor magnet 32 from dropping out, the following configuration is provided.

That is, as shown in FIG. 5, rotor magnet accommodating portion 24 is provided with a protruding portion 26, which is extended downwardly from the lower side of the base end portion 18, and a holding flange portion 28, which includes an enlarged tip of the protruding portion 26.

In addition, an installation portion 30 includes these protruding portion 26 and holding flange portion 28.

Moreover, the protruding portion 26 of the installation portion 30 is inserted in a setting 32b of the rotor magnet 32 including the annular permanent magnet.

As a result, by the enlarged holding flange portion 28, the turn stop of the rotor magnet 32 and the fall of the rotor magnet 32 are prevented against the impeller member 16.

In this case, as for the enlarged holding flange portion 28, after inserting the protruding portion 26 of the installation portion 30 into the setting 32b of the rotor magnet 32, for instance, by welding the tip of protruding portion 26 of installation portion 30, the enlarged holding flange portion 28 may be formed.

Moreover, in this welding, it is desirable that, between the rotor magnet 32 and the enlarged holding flange portion 28, the axial clearance is formed, in order to attain the above-mentioned abnormal sound prevention.

Moreover, in the centrifugal pump 10 of this Embodiment 4, the rotor magnet 32 is of a cylindrical shape as well as the centrifugal pump 10 of Embodiment 2.

In addition, between an outside diameter side 15a of a lower side 15 of the bearing portion 14 of the impeller member 16 and an inside diameter side 32a of the rotor magnet 32, only radial clearance V5 is formed.

As a result, swinging of the rotor magnet 32 can be absorbed by the clearance, which includes the radial clearance V5.

In addition, in the centrifugal pump 10 of Embodiment 1, to the protruding portion 38a, which is projected downwardly to the central portion of the top wall 38 of the upper main body casing 36, the upper bearing member 78 is fixed by the fixing holder 71, so that it is protruded downwardly in the inner periphery side opening portion 76 of the extending portion 74 of the blade casing 68.

On the shaft hole 80 formed in the upper bearing member 78, the top portion of the axial member 64, which passes through an inside of the bearing portion 14 of the rotating blade member 12, is fixed as pivoted.

On the contrary, in the centrifugal pump 10 of this Embodiment 4, such upper bearing member 78 is not formed, and the top portion of the axial member 64 is not pivoted, and it is of so-called cantilever form.

Moreover, in the centrifugal pump 10 of this Embodiment, an end portion portion 14a of the bearing portion 14 is protruded upwardly from the inner periphery side opening portion 76 of the extending portion 74 of the blade casing 68 such that it is exposed to the fluid introducing passage 84.

By the configuration like this, according to the rotational movement of the impeller member 16, the fluid easily enters into the interior space S1 and the rotating accommodating space S2 through inner periphery side opening portion 76 that is the flowing-in hole.

As a result, the fluid loss can be reduced.

Embodiment 5

Figure 6:
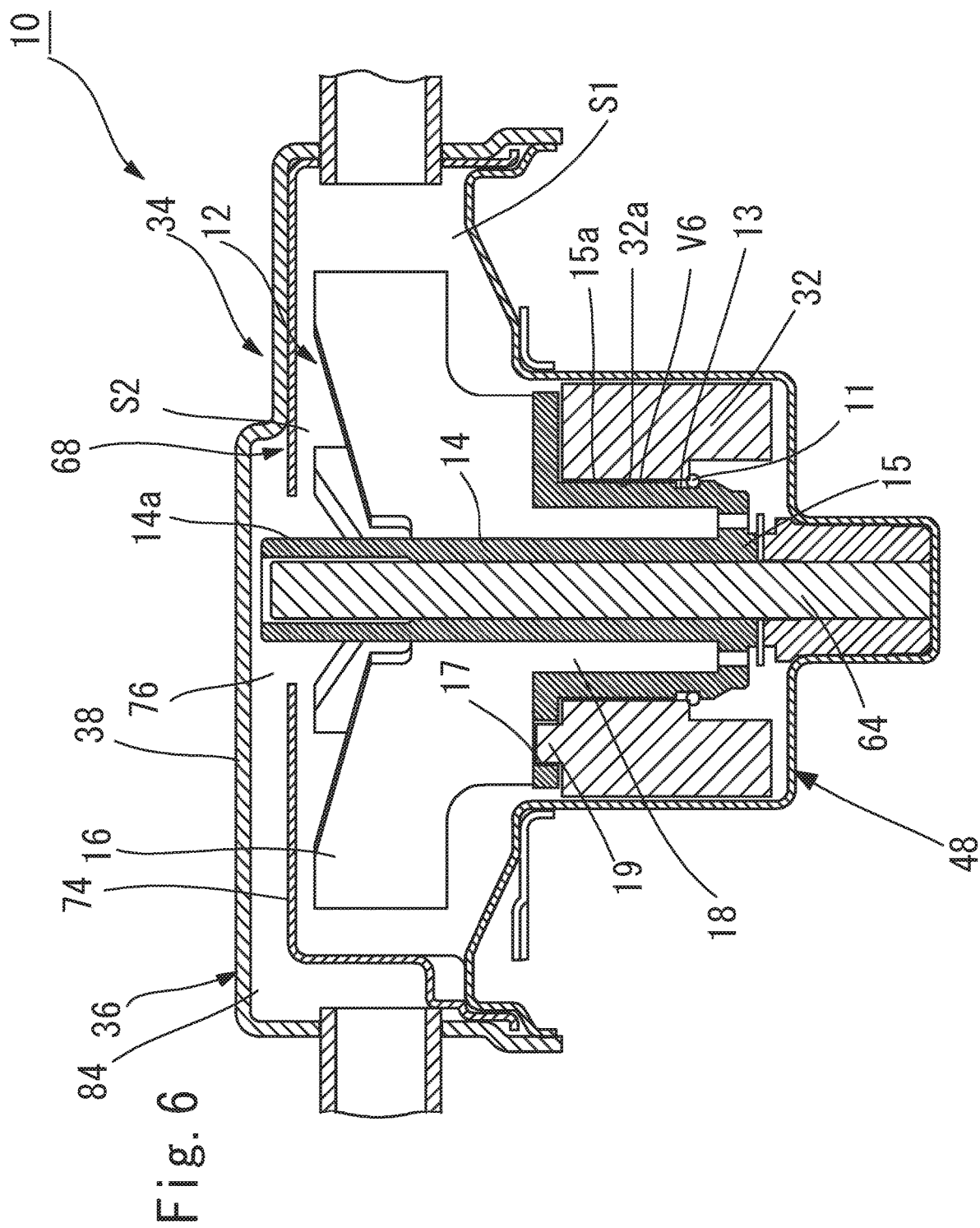
FIG. 6 is a vertical cross sectional view that shows Embodiment 5 of the centrifugal pump.

FIG. 6 is a vertical cross sectional view that shows Embodiment 5 of the centrifugal pump.

The centrifugal pump 10 of this Embodiment includes basically similar composition of the Embodiment shown in FIG. 1-FIG. 2.

The same reference numerals refer to the same composition members, and the detailed explanation is omitted.

In the centrifugal pump 10 of Embodiment 1, to the protruding portion 38a, which is projected downwardly to the central portion of the top wall 38 of the upper main body casing 36, the upper bearing member 78 is fixed by the fixing holder 71, so that it is protruded downwardly in the inner periphery side opening portion 76 of the extending portion 74 of the blade casing 68.

On the shaft hole 80 formed in the upper bearing member 78, the top portion 82 of the axial member 64, which passes through the bearing portion 14 of the rotating blade member 12, is fixed as pivoted.

On the contrary, in the centrifugal pump 10 of this Embodiment 5, such upper bearing member 78 is not formed, and the top portion of the axial member 64 is not pivoted, and it is of so-called cantilever form.

Moreover, in the centrifugal pump 10 of this Embodiment, as well as the centrifugal pump 10 of Embodiment of FIG. 4, as the dropout preventing means to prevent the impeller member 16 and the rotor magnet 32 from dropping out, the groove 13, which is formed at the rotor magnet accommodating portion 24 of the impeller member 16, is provided, and the snap ring 11 is provided at the groove 13 and it is engaged.

Furthermore, the engagement hole 17 is formed at the lower end of the base end portion 18 of the impeller member 16, and the protruding portion 19, which is formed on the top of the rotor magnet 32, is fitted to this engagement hole 17.

As a result, the rotation transmission portion is configured and the turn stop of the rotor magnet 32 and the fall of the rotor magnet 32 are prevented against the impeller member 16.

Furthermore, in the centrifugal pump 10 of this Embodiment 4, as well as the centrifugal pump 10 of Embodiment 2, the rotor magnet 32 is of a cylindrical shape.

Moreover, between an outside diameter side 15a of a lower side 15 of the bearing portion 14 of the impeller member 16 and an inside diameter side 32a of the rotor magnet 32, only radial clearance V6 is formed.

As a result, swinging of the rotor magnet 32 can be absorbed by the clearance, which includes the radial clearance V6.

Although preferable embodiment is described above, embodiments are not limited to that embodiment.

For instance, in the above-mentioned Embodiments, materials of the main body casing 34, the upper main body casing 36, the lower main body casing 48, and the blade casing 68, etc. may be made of metallic, or may be made of plastic, and it may be selected appropriately according to the usage, and it is not limited particularly.

In addition, in the Embodiment, the number of the suction side coupling member 42 and the number of the discharge side coupling member 46 are assumed to be one, respectively.

However, the number of suction side coupling members 42 and the number of discharge side coupling members 46 can be plural.

Therefore, various changes are possible in the scope.

INDUSTRIAL APPLICABILITY

Embodiments can be applied to a centrifugal pump and a method of producing of the centrifugal pump to circulate the fluid in the closed circuit, for instance, refrigerant used for refrigerant circulation circuits such as air conditioners and freezers, and cooling water, etc. used for cooling circulation circuits for parts and apparatuses that generate heat, etc.

EXPLANATION OF LETTERS OR NUMERALS

10 Centrifugal pump
11 Snap ring
12 Rotating blade member
13 Groove
14 Bearing portion
14a End portion
15 Lower side
15a Outside diameter side
16 Impeller member
17 Engagement hole
18 Base end portion
18a Lower end
18b Outside diameter side
19 Protruding portion
20 Enlarged diameter portion
22 Outside blade portion
24 Rotor magnet accommodating portion
26 Protruding portion
28 Holding flange portion
30 Installation portion
31 Outer periphery cylindrical portion
31a Inside diameter side
32 Rotor magnet
32a Inside diameter side
32b Setting hole
33 Upper surface
34 Main body casing
36 Upper main body casing
38 Top wall
38a Protruding portion
40 Side peripheral wall
42 Suction side coupling member
46 Discharge side coupling member
48 Lower main body casing
51 Lower end part
52 Outer periphery flange
54 Blade accommodating portion
56 Rotor magnet accommodating portion
58 Lower bearing member accommodating portion
60 Lower bearing member
62 Shaft hole
64 Axial member
66 Lower end portion
68 Blade casing
70 Outer periphery flange
71 Fixing holder
72 Side peripheral wall
74 Extending portion
76 Inner periphery side opening portion
78 Upper bearing member
80 Shaft hole
82 Top portion
84 Fluid introducing passage
100 Centrifugal pump
102 Rotating blade member
104 Bearing portion
106 Impeller member
106a Inside diameter side
108 Base end portion
110 Enlarged diameter portion
112 Outside blade portion
122 Rotor magnet
124 Main body casing
126 Upper main body casing
128 Top wall 128a Protruding portion
130 Side peripheral wall
132 Suction side coupling member
136 Discharge side coupling member
138 Lower main body casing
141 Lower end part
142 Outer periphery flange
144 Blade accommodating portion
146 Rotor magnet accommodating portion
148 Lower bearing member accommodating portion
150 Lower bearing member
152 Shaft hole
154 Axial member
156 Lower end portion
158 Blade casing
160 Outer periphery flange
161 Fixing holder
162 Side peripheral wall
164 Extending portion
164a Inner periphery side opening portion
168 Upper bearing member
170 Shaft hole
172 Top portion
174 Fluid introducing passage
186 Main body casing side fixing bracket
204 Coil portion
206 Bobbin casing
208 Winding wire
210 Coil
214 Coil cover main body
216 Coil side fixing protruded portion
226 Connector
228 Lead line
230 Magnetic pole sensor
240 Screw member
O Rotation central axis
S1 Interior space
S2 Rotating accommodating space
V1~V6 Clearance

What is claimed:

1. A centrifugal pump comprising:
 a rotating blade member including an impeller member and a rotor magnet associated with the impeller member, wherein the impeller member includes a blade;
 a main body casing in which the rotating blade member is accommodated;
 a coil portion that rotates the rotating blade member, wherein the coil portion is located on a periphery of the rotor magnet; and
 an axial member which is associated with the main body casing, wherein the rotating blade member pivots around the axial member,
 wherein a clearance, in which the rotor magnet is allowed to move, is provided between the blade and the rotor magnet, and
 wherein the clearance between the blade and the rotor magnet includes a radial clearance r between the blade and the rotor magnet and an axial clearance h between the blade and the rotor magnet, and r is smaller than h.

2. The centrifugal pump of claim 1, further comprising: a dropout preventing means to prevent the impeller member and the rotor magnet from dropping out.

3. The centrifugal pump of claim 1, wherein the main body casing has a first end and a second end in an axial direction of the axial member, and the axial member is fixed at the first end and the second end.

4. The centrifugal pump of claim 1, wherein the main body casing has a third end at a side of the rotor magnet, and the axial member is fixed at the third end.

5. The centrifugal pump of claim 1, wherein the blade includes a first blade part, a second blade part, and a third blade part,
 the second blade part is placed between the first blade part and the third blade part,
 a first length of the first blade part in a radial direction perpendicular to the axial member is shorter than a second length of the second blade part in the radial direction, and
 a second length of the second blade part in the radial direction is shorter than a third length of the third blade part in the radial direction.

6. The centrifugal pump of claim 5, wherein the rotor magnet is associated the first blade part and the second blade part.

* * * * *